(12) United States Patent
Shadduck

(10) Patent No.: US 10,555,802 B1
(45) Date of Patent: Feb. 11, 2020

(54) UROLOGIC STENTS AND METHODS OF USE

(71) Applicant: John H. Shadduck, Menlo Park, CA (US)

(72) Inventor: John H. Shadduck, Menlo Park, CA (US)

(*) Notice: Subject to any disclaimer, the term of this patent is extended or adjusted under 35 U.S.C. 154(b) by 0 days.

(21) Appl. No.: 16/296,019

(22) Filed: Mar. 7, 2019

(51) Int. Cl.
*A61F 2/04* (2013.01)
*A61M 27/00* (2006.01)

(52) U.S. Cl.
CPC ............ *A61F 2/04* (2013.01); *A61M 27/008* (2013.01); *A61F 2002/047* (2013.01); *A61F 2002/048* (2013.01)

(58) Field of Classification Search
CPC ................ A61F 2/08; A61F 2/82; A61F 2/92
USPC ............................... 623/1.1–1.48, 23.65–23.7
See application file for complete search history.

(56) References Cited

U.S. PATENT DOCUMENTS

| | | | |
|---|---|---|---|
| 6,217,609 B1 * | 4/2001 | Haverkost | A61F 2/90 623/1.13 |
| 6,475,232 B1 * | 11/2002 | Babbs | A61F 2/07 623/1.13 |
| 6,746,489 B2 * | 6/2004 | Dua | A61F 2/04 623/23.68 |
| 8,016,879 B2 * | 9/2011 | Gale | A61L 31/146 623/1.39 |
| 9,333,102 B2 * | 5/2016 | Yachia | A61F 2/90 |
| 9,345,816 B2 * | 5/2016 | Gale | A61L 31/146 |
| 9,843,854 B2 * | 12/2017 | Keady | H04R 1/1091 |
| 9,943,323 B2 * | 4/2018 | Martin | A61F 2/06 |
| 2008/0071307 A1 * | 3/2008 | DeBruyne | A61F 2/07 606/200 |
| 2009/0270971 A1 * | 10/2009 | Xiao | A61F 2/07 623/1.14 |
| 2010/0023046 A1 * | 1/2010 | Heidner | A61B 17/12036 606/191 |
| 2010/0069916 A1 * | 3/2010 | Cully | A61F 2/07 606/108 |
| 2012/0143306 A1 * | 6/2012 | Cully | A61F 2/07 623/1.13 |
| 2012/0150277 A1 * | 6/2012 | Wood | A61F 2/90 623/1.15 |
| 2017/0135803 A1 * | 5/2017 | Moon | A61F 2/04 |

* cited by examiner

*Primary Examiner* — Suzette J Gherbi

(74) *Attorney, Agent, or Firm* — Levine Bagade Han LLP

(57) ABSTRACT

Urologic stents that are adapted for temporary use to provide relief following treatments for benign prostatic hyperplasia and other disorders of the prostate, urethra and ureters.

39 Claims, 20 Drawing Sheets

UROLOGIC STENTS AND METHODS OF USE

BACKGROUND OF THE INVENTION

1. Field of the Invention

This invention relates to urologic stents that are adapted for temporary use to provide relief following treatments for benign prostatic hyperplasia and other disorders of the prostate, urethra and ureters.

2. Description of the Background Art

Bladder outlet obstruction is a common disorder in urology which is most frequently caused by benign prostatic hyperplasia (BHP). The prostate gland is approximately the size of a chestnut in younger men and surrounds the urethra just below the bladder neck. As men age, the prostate gland increases in size and constricts the urethra which obstructs the normal flow of urine from the bladder. Benign prostatic hyperplasia is common and typically begins to develop in males older than 50. As many as 60% of men by age 60 have bothersome BPH symptoms and 80% of men by age 80 experience bladder outlet obstruction due to BPH.

Various surgical treatments have been developed for resection or ablation of prostate tissue to thereby reduce or eliminate urethral constriction to improve the patient's quality of life. For example, BPH treatments include transurethral resection of the prostate (TURP), laser prostatectomy, convective vapor ablation which delivers thermal energy stored in water vapor to ablate prostate tissue (the Rezum® system) and other experimental and emerging procedures.

If left untreated, urinary retention can have serious consequences for the patient including kidney failure. Therefore, patients with chronic or acute urinary retention usually require some type of intervention. Following a surgical procedure, it is very common for the patient to be catheterized with an indwelling catheter, such as a Foley catheter, which provides a temporary conduit for draining the bladder. A Foley catheter is equipped with an inflatable balloon that functions as an anchoring means within the bladder. The catheter traverses the entire urethra from the bladder and includes a segment that protrudes externally from the patient. Such Foley catheters are used for temporary relief while the patient is recovering from most types of prostate surgery.

More recently, prostatic stents have been designed which do not traverse the entire length of the patient's urethra. The stents typically consist of a tubular section that spans a portion of the prostatic urethra with proximal and distal anchoring means to prevent migration, and typically a tether for the removal of the stent. In any prostatic stent, migration of stent is a major problem and most stents are equipped with an inflatable balloon that functions as an anchoring means in the bladder as in a Foley catheter. For example, Whalen et al. in U.S. Pat. No. 7,141,038 describe a prostatic stent with a balloon for anchoring the device in the bladder with a compressible segment that spans the external sphincter and another balloon anchor in the penile urethra just below the external sphincter. Lazarovitz et al. in U.S. Pat. No. 6,716,252 describe a prostatic stent adapted for use in the prostatic urethra that has an inflatable balloon functioning as an anchor in the bladder. This stent also includes a distal end that adapted for positioning above the external sphincter which may prevent the stent from migrating toward the bladder. Other prostatic stent designs with a balloon anchor in the bladder and other anchor means below the external sphincter include Whalen, et al., in U.S. Pat. Nos. 6,991,596 and 7,108,655. All the prostatic stents with proximal anchoring balloons and distal anchor mechanisms are complex and expensive to manufacture.

SUMMARY OF THE INVENTION

The present invention relates to a stent which is designed for temporary use and would typically be used following a surgical intervention for treating BPH, prostate cancer or another prostate disorder. The prostatic stent corresponding to the invention allows for drainage of urine from the bladder by providing a stent passageway within a portion of the prostatic urethra while leaving the prostate external sphincter unaffected so that the patient is able to control urination in a normal manner. The prostatic stent disclosed herein comprises a temporary indwelling device which spans the prostatic urethra thereby facilitating drainage of urine from the bladder. In other variations, a stent corresponding to the invention can be used to treat strictures and other disorders of the bulbous urethra and ureters.

One example of a stent for treating a urologic disorder includes a stent body having a deployed configuration with an outer surface portion having a plurality of projecting elements directed outward from the outer surface portion such that the plurality of projecting elements are configured to engage tissue in a wall of a lumen in a patient's urinary tract, wherein the stent body has a central passageway extending therethrough; and wherein the stent body is transformable to an inverted configuration in which the outer surface portion is configured to invert within an end of the stent causing movement of the projecting elements within the central passageway of the stent body which disengages the projecting elements from the tissue for withdrawal of the stent body from the lumen.

A variation of the stent can include a stent body dimensioned for deployment in a lumen of a prostatic urethra, a ureter or a bulbous urethra.

Variations of the stent can further include a tether coupled to the stent body such that application of a force on the tether causes transformation of the stent body from the deployed configuration to the inverted configuration. In some variations, distal movement of the tether is adapted to progressively roll and invert the outer surface portion to the inverted configuration.

The stents described herein can include an outer surface portion carrying the projecting elements and further include comprises a tear-away portion. Optionally, the tether can be coupled to the tear-away portion.

Variations of the stents can include at least one spring element that reinforces the central passageway and prevents collapse thereof in the deployed configuration. At least a portion of the spring element can be in a helical configuration. Typically, the spring element is radially-collapsible to allow radial compression of thereof.

The stents disclosed herein can include a stent body with a cylindrical configuration about a central axis. For example, the stent body can extend about an axis from a proximal end to a distal end and has an expanded cross section in a medial portion between the proximal and distal ends. In additional variations, the stent body has a round cross-sectional shape. The stent body can further include a stent body with a partially triangular cross-sectional shape.

The stents disclosed herein can include a plurality of openings in a wall of the stent body.

In another variation, stents described herein can include a stent body having an insertion configuration with an outer sleeve portion surrounding an inner body portion having a central passageway extending therethrough; wherein the stent body is adaptable to an inverted configuration in which the sleeve portion rolls and inverts within the central passageway to allow for withdrawal from the lumen.

The stents disclosed herein can be dimensioned for insertion and deployment in a prostatic urethra, a ureter or a bulbous urethra.

In another variation, stents can include an elongated tether coupled to the inner body portion. Optionally, the stent can be configured such that distal movement of the tether causes a progressive rolling of the sleeve portion to invert within the central passageway to assume the inverted configuration.

The stents disclosed herein can include an exterior surface of the everted sleeve portion that has at least one engagement feature that engages a wall of a lumen.

The present disclosure includes methods for temporarily stenting a urinary tract lumen. For example, one such method includes deploying a stent body in a urinary tract lumen for a treatment interval wherein an outer surface portion of the stent body carries projecting elements that engage a tissue in a wall of the urinary tract lumen; and disengaging the projecting elements from tissue by pulling distally on a tether coupled to a portion of the stent body to cause the outer surface portion of the stent body to invert within the stent body such that the projecting elements face inwardly allowing for withdrawal of the stent body from the urinary tract lumen.

The methods can include disengaging the projecting elements from tissue by inverting a tear-away outer surface portion of the stent body. Disengaging the projecting elements from tissue can be performed by inverting a sleeve portion of the stent body.

Another variation of a method includes methods for treating a wall of a lumen to treat a urologic disorder. For example, such a method can include providing a delivery catheter carrying a stent body having a insertion configuration with an outer surface carrying projecting elements that engage tissue in the wall of the lumen, the stent body having a passageway extending therethrough; introducing a distal portion of the catheter into the lumen; deploying the stent body from the catheter in the insertion configuration to create a temporary flow path through the stent passageway and lumen; withdrawing the catheter from the lumen; subsequent to a treatment interval, pulling distally on a tether coupled to a portion of the stent body to invert the outer surface portion carrying the projecting elements within the stent body allowing for disengaging the stent body from the lumen; and withdrawing the stent body from the lumen after inverting the outer surface portion.

Variations of the method can include introducing the distal portion by expanding an expandable member carried at a distal end of the catheter in a patient's bladder and positioning the expandable member in the bladder proximate the internal sphincter. Collapsing the expandable member can occur prior to withdrawing the catheter from the lumen. The methods can include introducing the distal portion of the catheter into a prostatic urethra, a ureter or a bulbous urethra.

Figures 5A, 5B:
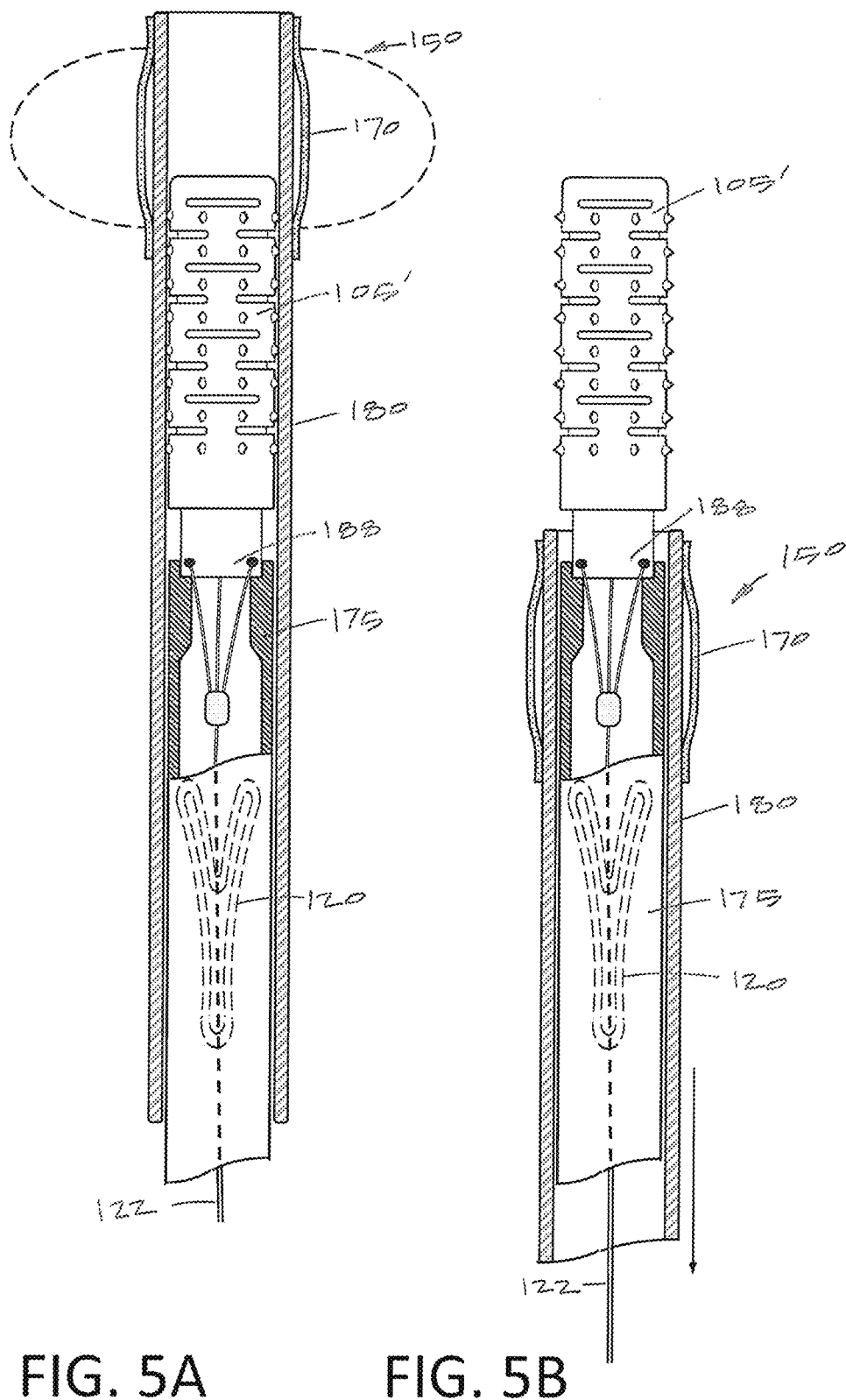
FIG. 5A shows the stent of FIG. 4 loaded in a catheter prior to deployment.

The 5B shows the stent in the catheter of FIG. 5A with an outer sleeve of the catheter being withdrawn to thereby deploy the stent.

Figures 1A, 1B:
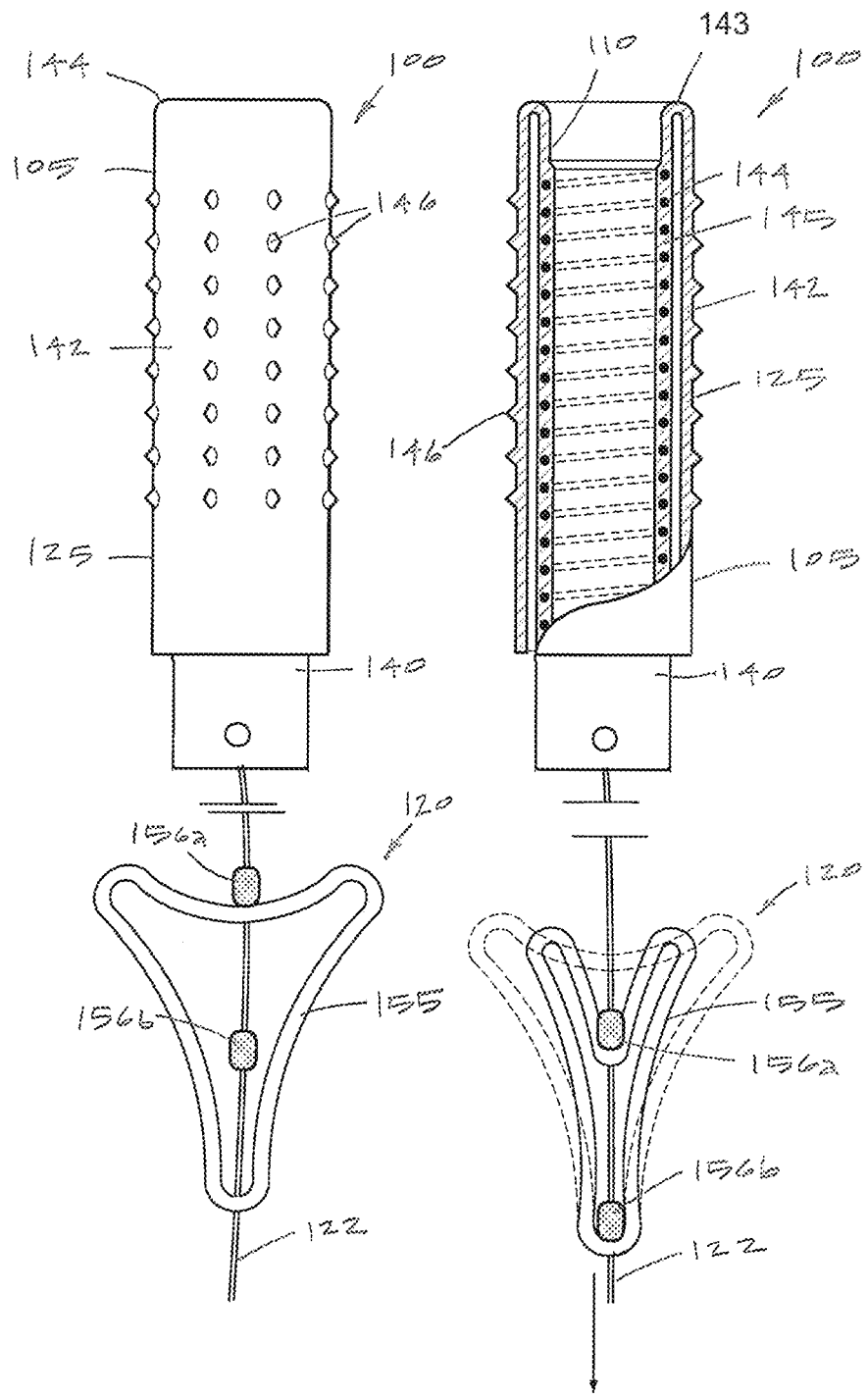
FIG. 1A is an elevational view of a prostatic stent of the invention with a stent body having gripping features and an optional anchor that can be positioned in the patient's urethra distal to the external sphincter of the prostate.
FIG. 1B is the cut-away view of the stent of FIG. 1A with an everted outer sleeve portion that is folded or everted over the inner tubular stent body portion.
Figures 6A, 6B:
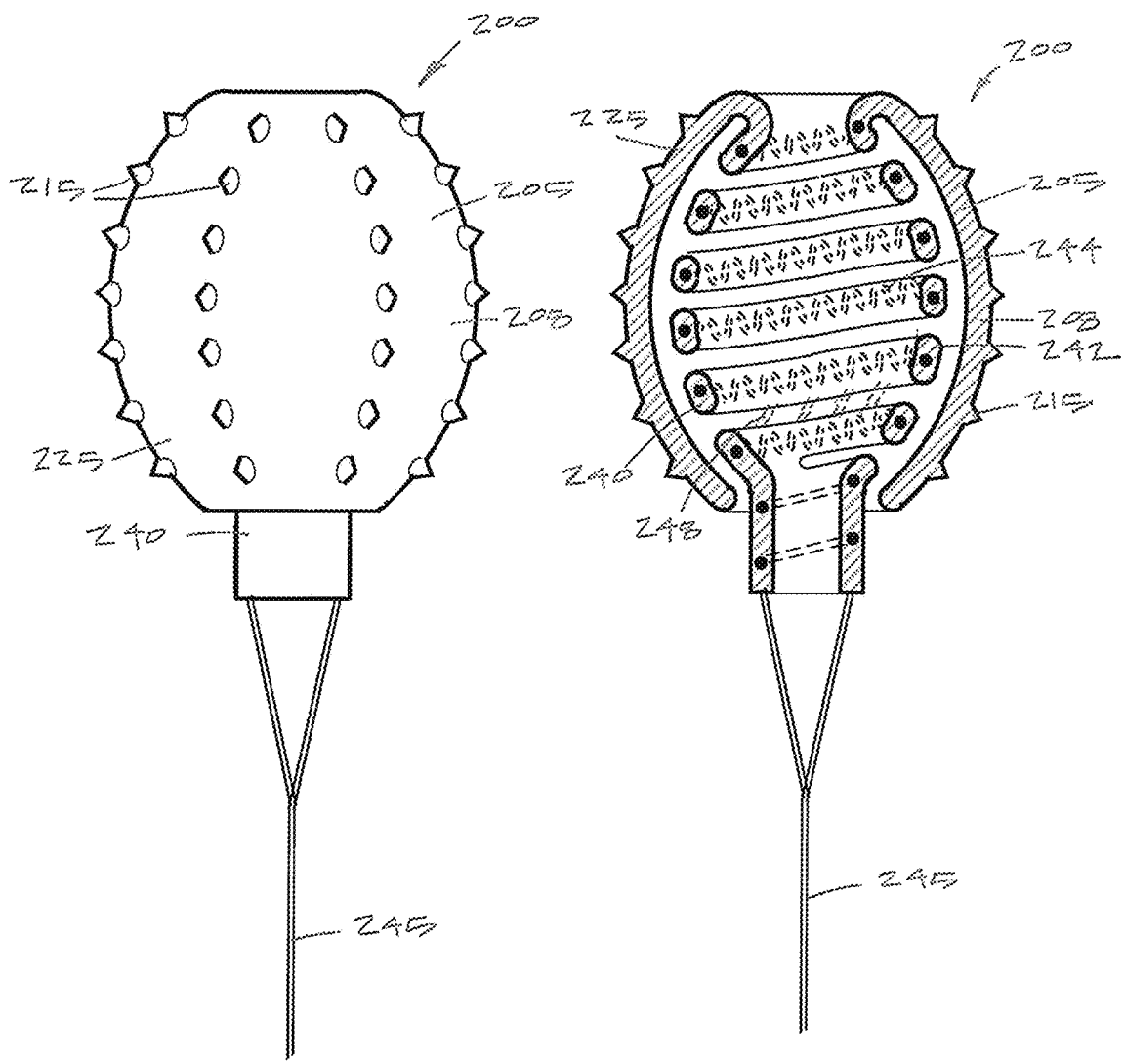

FIG. 6A is an elevational view of a stent similar to that of FIG. 1A that has a bowed outward medial portion with projecting elements thereon for gripping or engaging tissue.

FIG. 6B is a sectional view of the stent of FIG. 6A showing an interior body portion that is radially collapsible with a spring element embedded in elastomeric walls thereof.

Figure 6C:
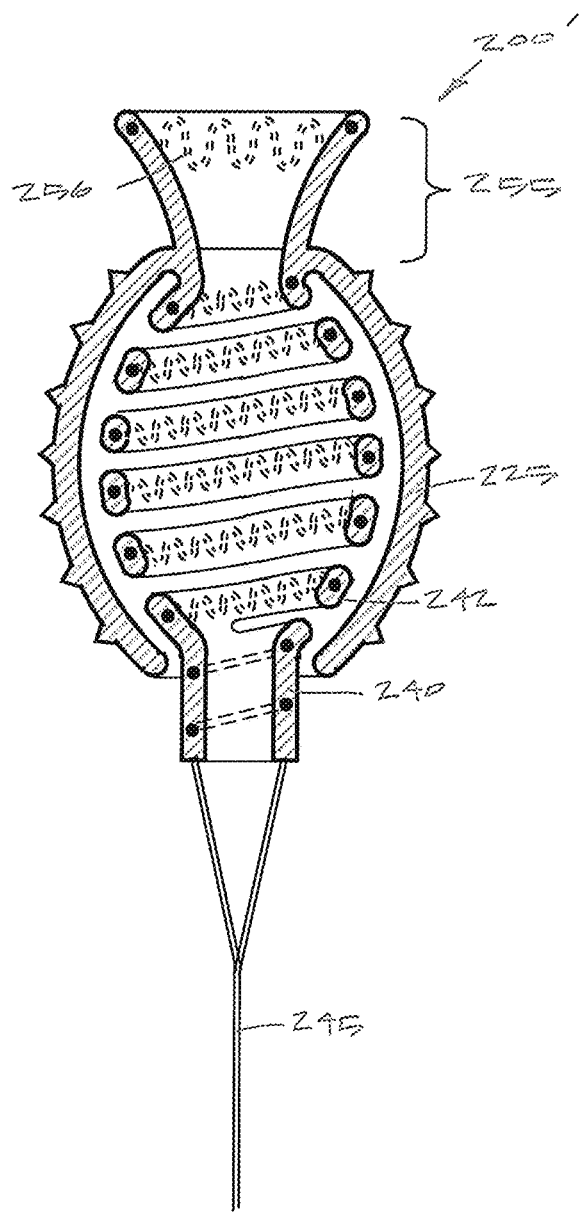

FIG. 6C is a sectional view of another variation of a stent similar to that of FIGS. 6A-6B that includes a collar portion adapted to extend into and engage the bladder wall at the internal sphincter to function as an anchor.

Figure 7:
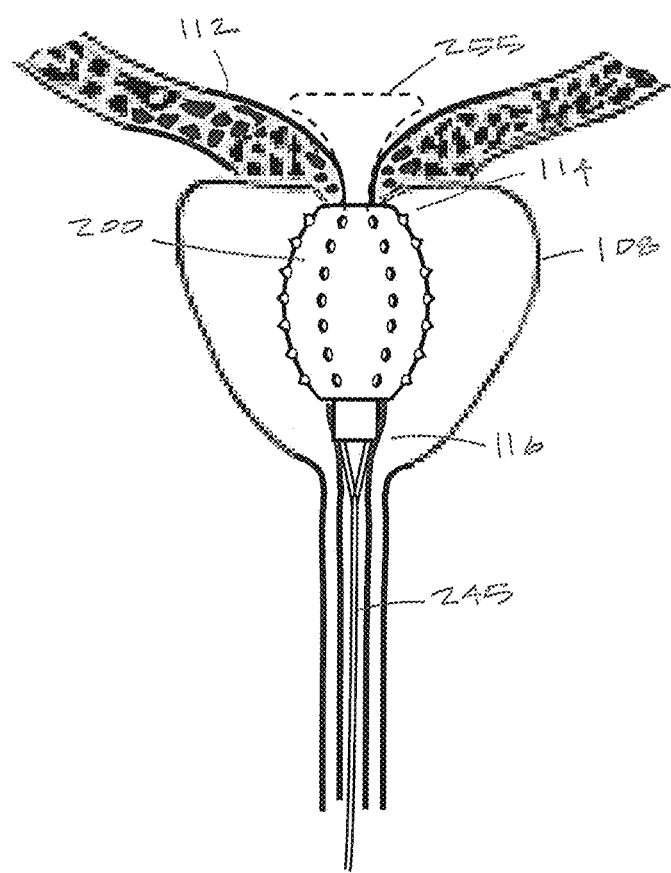

FIG. 7 is a schematic view of the stent of FIG. 6A deployed in a patient's prostatic urethra.

Figure 8:
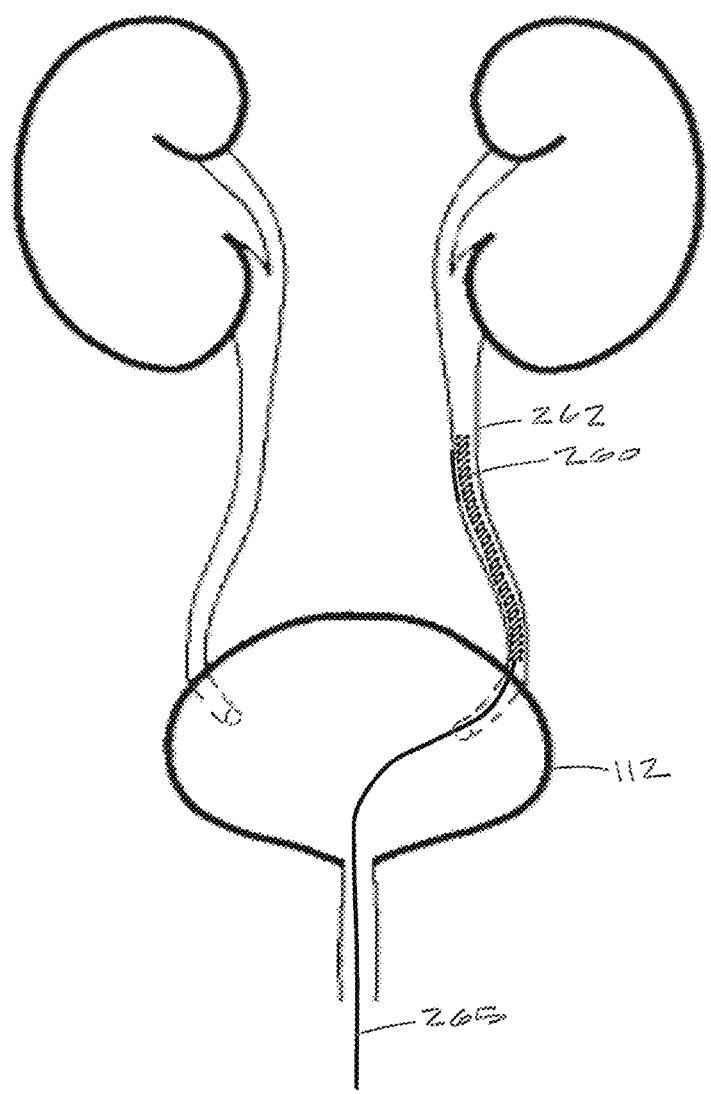

FIG. 8 is a schematic view of a stent variation similar to that of FIG. 1A configured for deployment in a patient's ureter.

Figure 9:
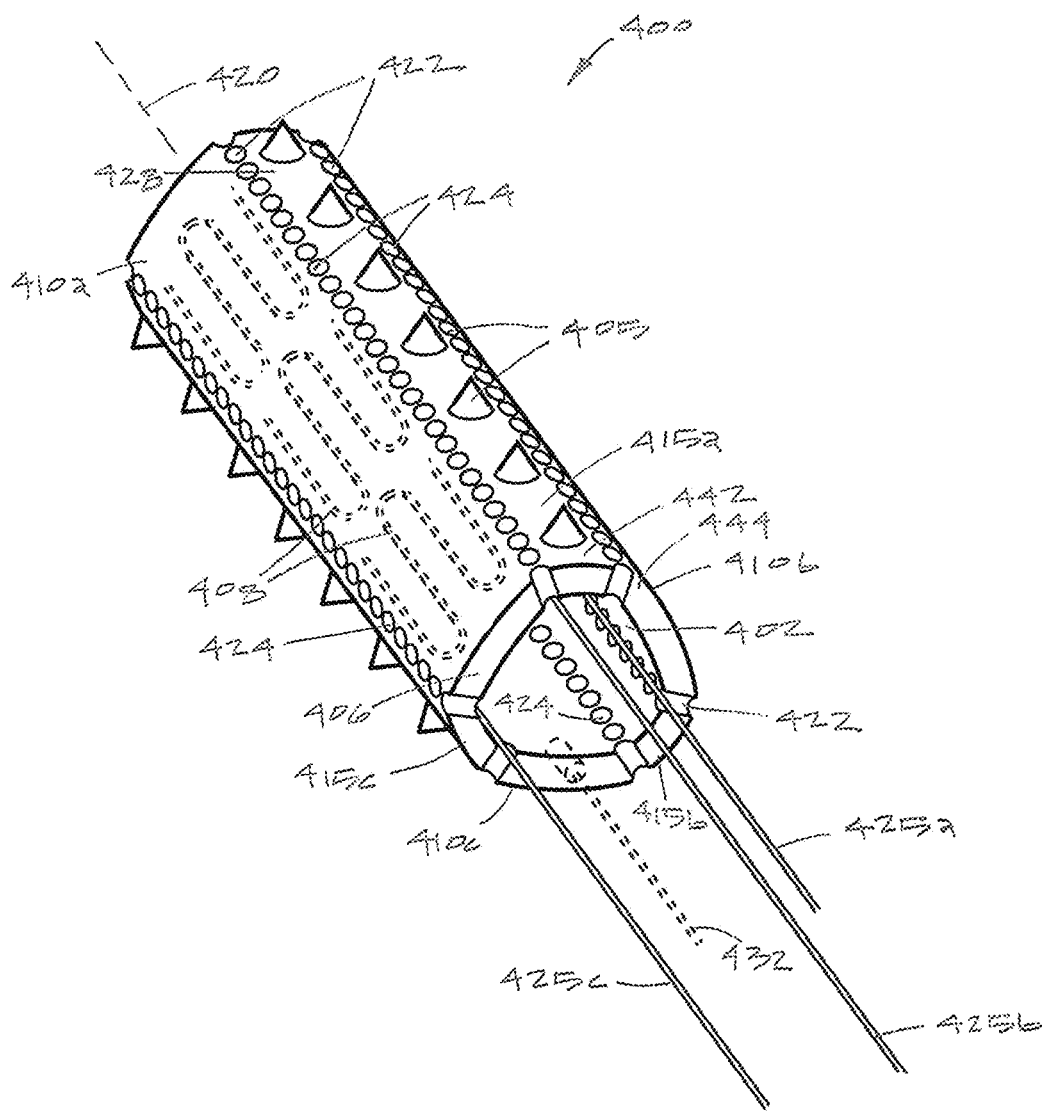

FIG. 9 is a perspective view of another variation of a stent that has elastomeric wall portions with spring elements therein that allow for radial compression of the stent for carrying in a catheter as well as projecting elements for gripping tissue, where the projecting elements are carried on longitudinal strips of the stent that can be inverted along tear-away lines on sides of the tear-away strips.

Figure 10:
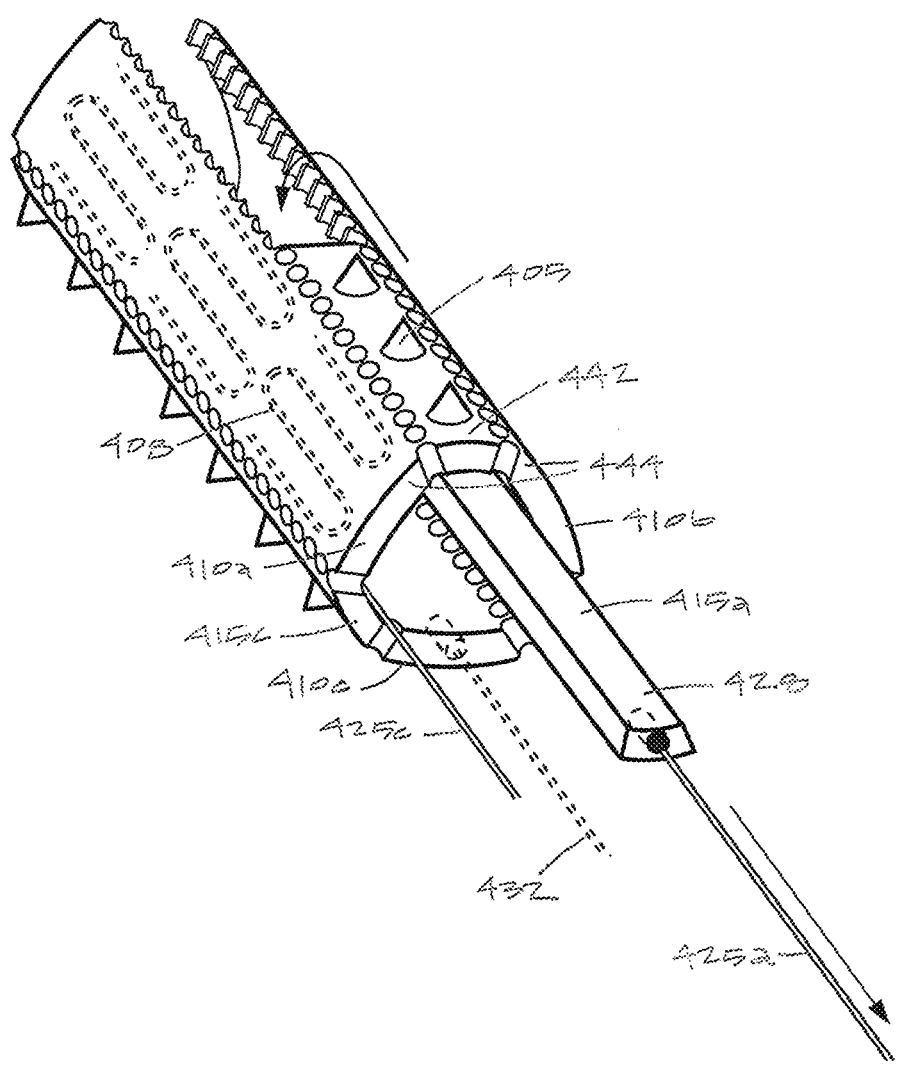

FIG. 10 is a view of the stent FIG. 9 after a tear-away strip of the stent is partly torn away.

Figure 11A:
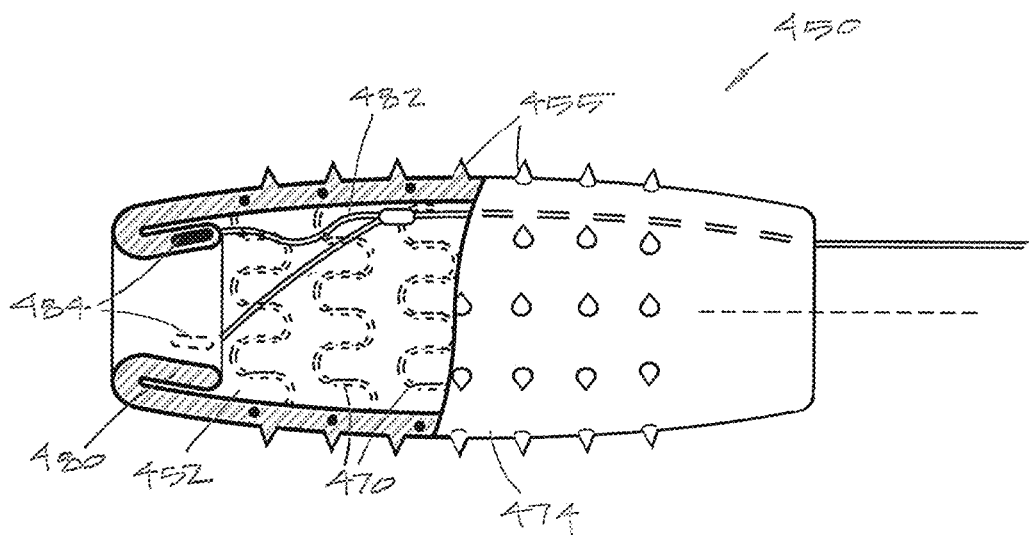

FIG. 11A is cut-away view of another variation of a stent with the outer surface having projecting elements for gripping tissue, where the stent again can be inverted for disengaging the projecting elements from tissue to thus allow simplified removal from the patient's urethra.

Figure 11B:
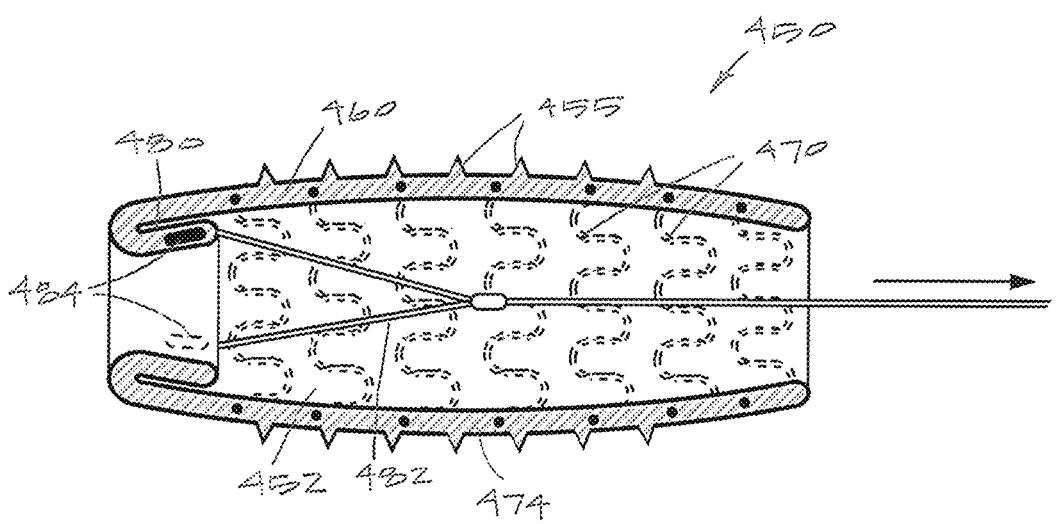

FIG. 11B is a sectional view of the stent of FIG. 11A showing the tether being tensioned for inverting wall of the stent to thus invert and remove the stent from the patient's urethra.

Figures 12A, 12B:
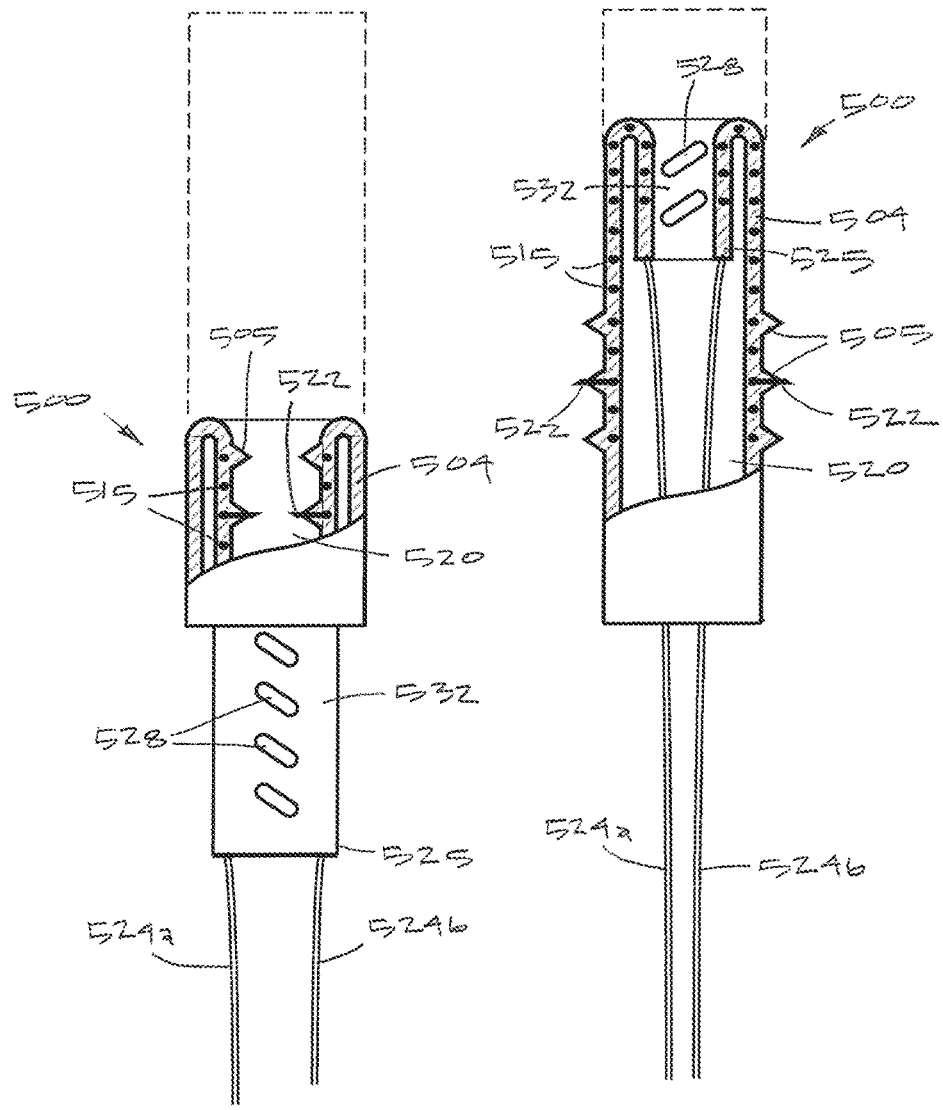

FIG. 12A is a cut-away view of another variation of temporary prostatic stent shown in a first pre-deployed configuration that is adapted for deployment by everting an elastomeric sleeve portion thereof.

FIG. 12B is another cut-away view of the prostatic stent of FIG. 12A shown in a second deployed configuration after everting a portion thereof to cause projecting elements to engage tissue.

Figure 13A:
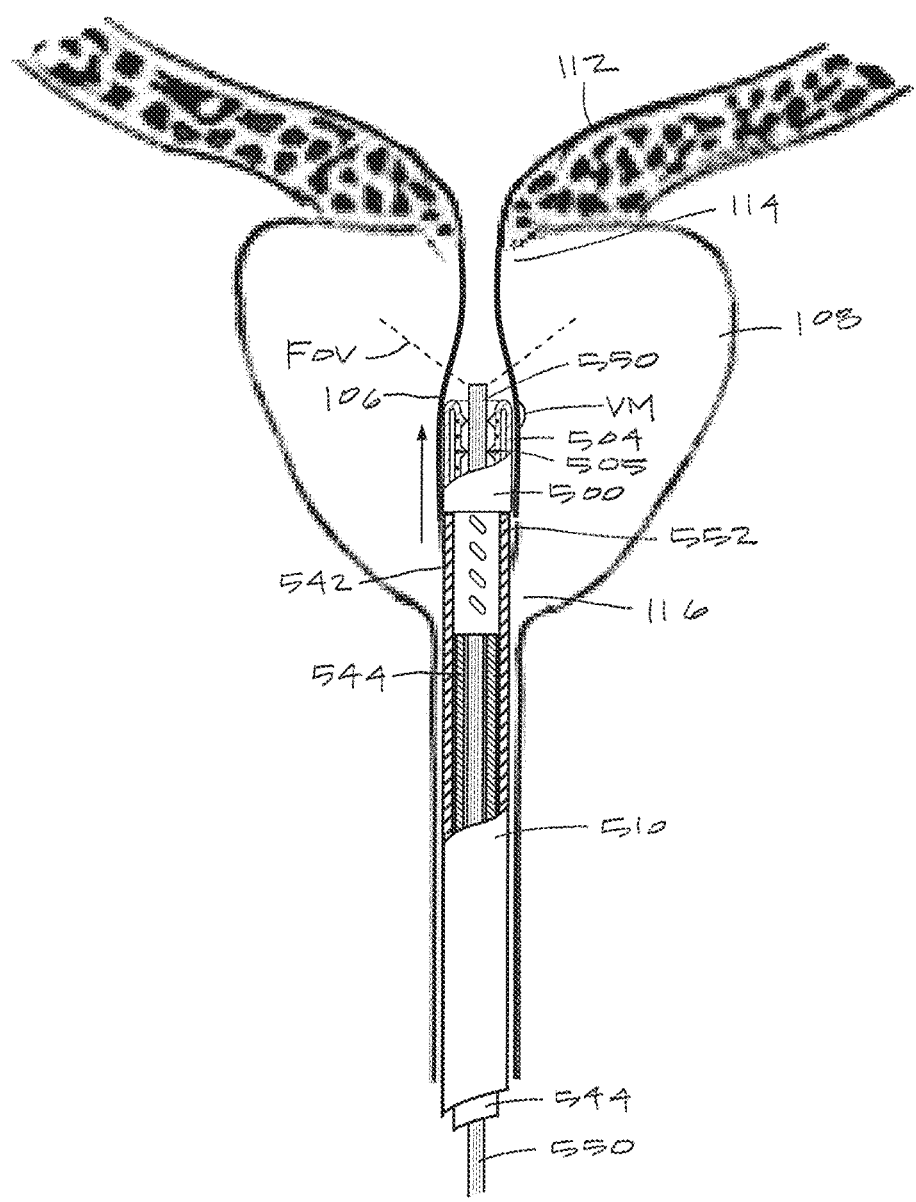

FIG. 13A illustrates a step of a method of introducing the stent of FIG. 12A in a transurethral approach under endoscopic vision to a site in a patient's prostate.

Figure 13B:
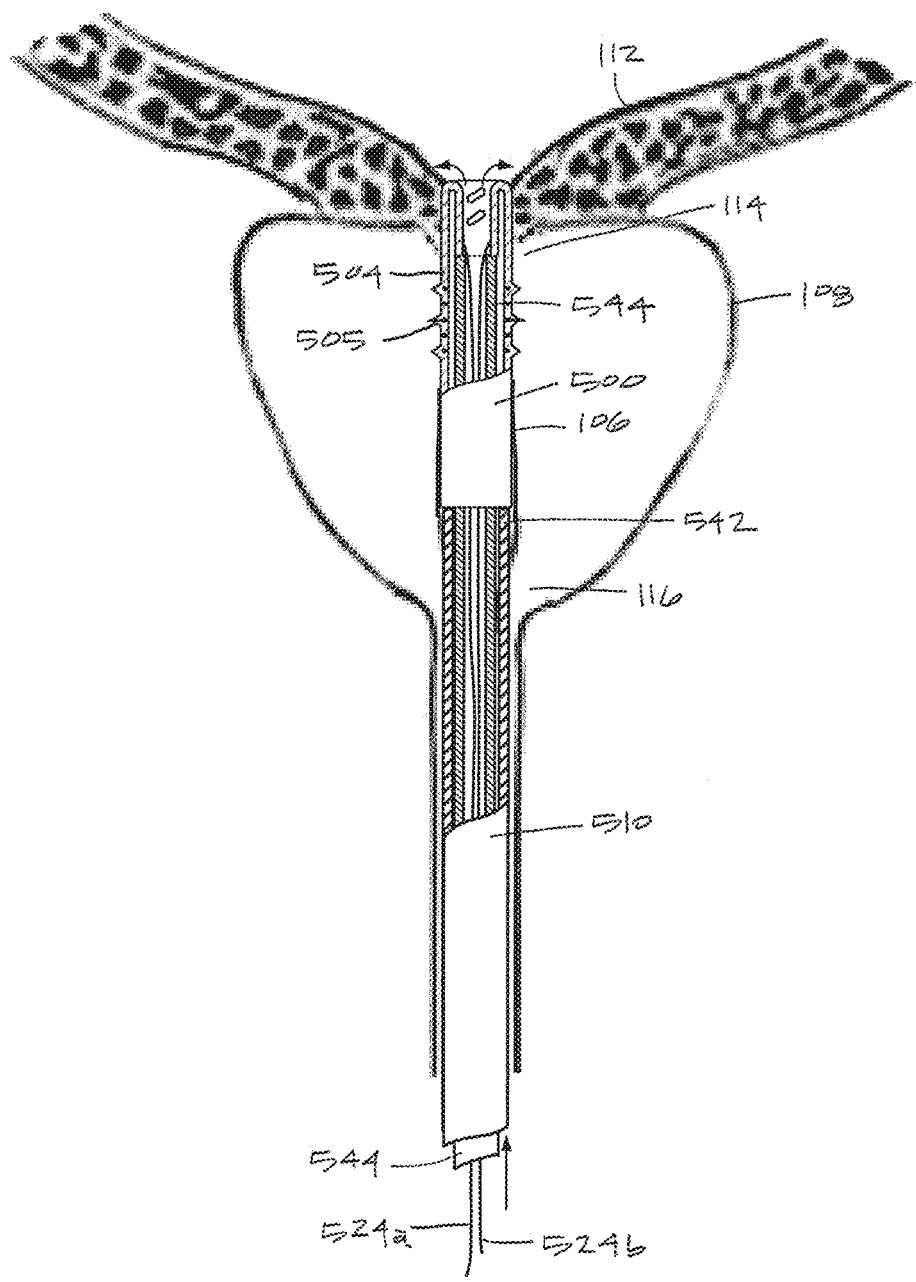

FIG. 13B illustrates a subsequent step of the method of FIG. 13A to evert and deploy the prostatic stent from a catheter.

Figure 13C:
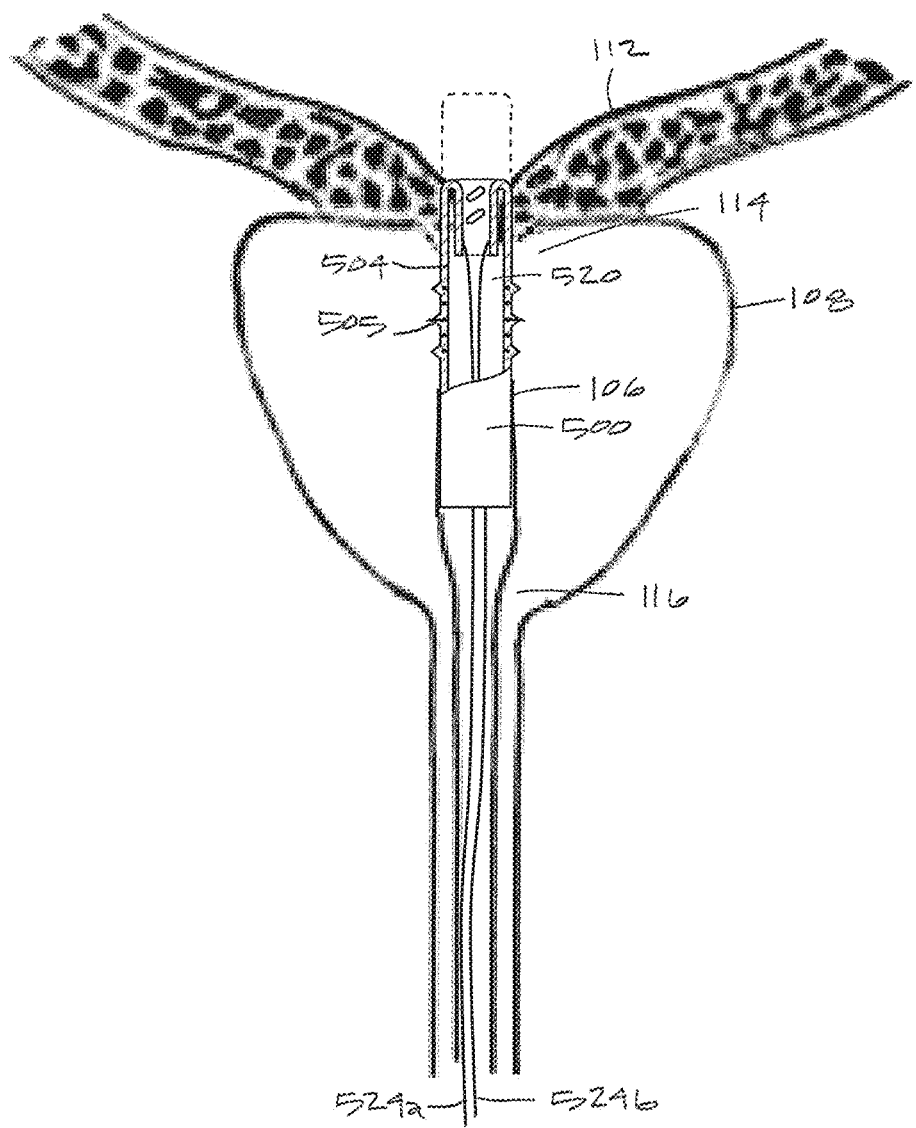

FIG. 13C illustrates another step of the method of FIGS. 13A-13B wherein prostatic stent is deployed and the catheter is removed.

Figure 13D:
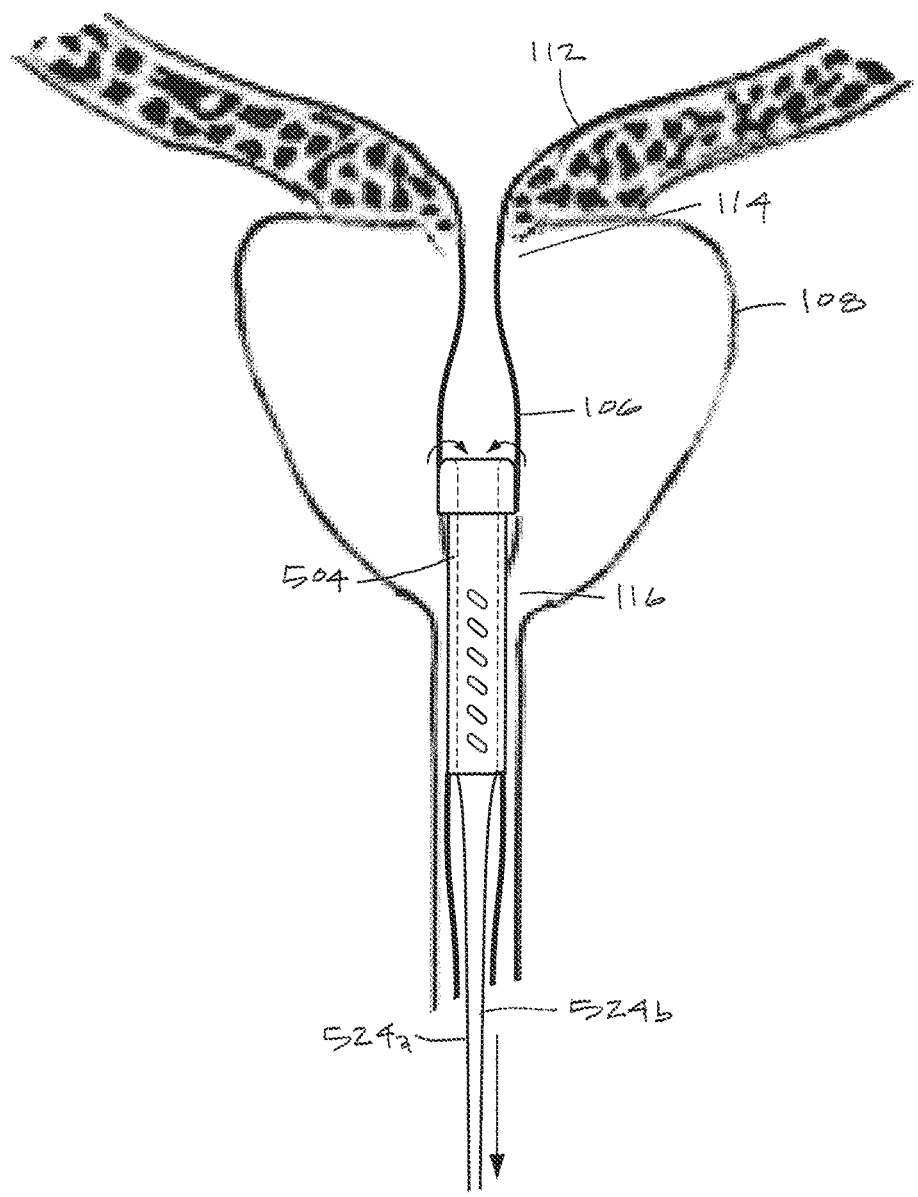

FIG. 13D illustrates another step of the above method wherein the prostatic stent is inverted by pulling distally on the tethers which disengages the projecting elements from tissue and allows for removal of the stent.

DETAILED DESCRIPTION

Figure 2B:
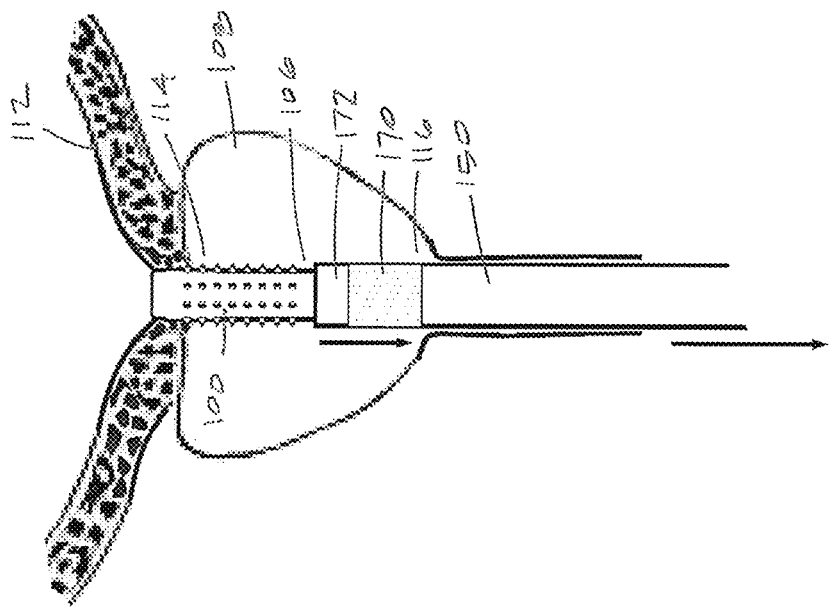
FIG. 2B illustrates the subsequent step wherein an outer sleeve of the catheter is withdrawn to deploy the stent of FIG. 1A in the patient's pro static urethra.
Figure 2A:
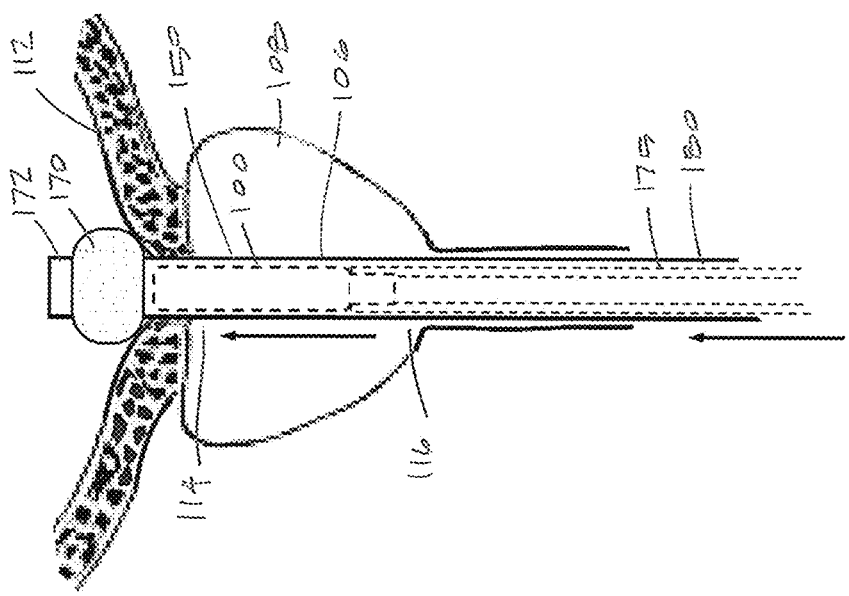
FIG. 2A is a schematic view of an initial step of a method of the invention wherein a catheter carrying the stent of FIG. 1A is introduced through the patient's urethra and a balloon at the distal end of the catheter is inflated in the patient's bladder.
Figure 2D:
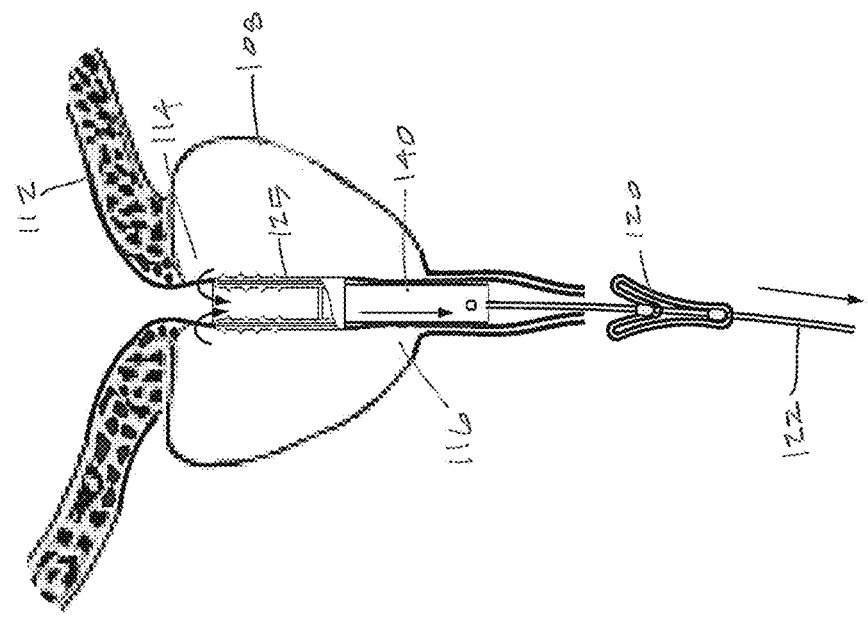
FIG. 2D illustrates removal of the stent wherein the distal movement of the tether collapses the anchor and begins to invert the outer sleeve portion of the stent.
Figure 2C:
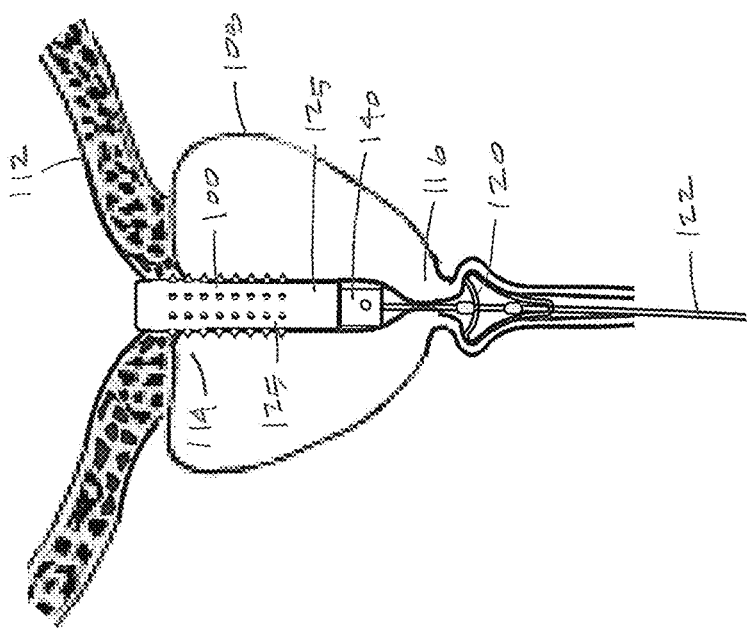
FIG. 2C shows the stent of FIG. 1A deployed with an anchor distal to the exterior sphincter of the prostate.

FIGS. 1A and 1B show a prostatic stent 100 of the present invention which consists of a stent body 105 adapted to span the prostatic urethra 106 when deployed in a patient's prostate 108 as shown in FIG. 2C. The stent is adapted for temporary use which may range from a few days to 1 month, and typically would be used for 1 week to two weeks. The stent body 105 has a non-collapsible central passageway 110 therein to allow urine drainage from the bladder 112 through the internal sphincter 114, prostatic urethra 106, external sphincter 116, bulbous urethra 118 and outwardly through the penile urethra (see FIG. 2C). An optional distal anchor 120 is shown in FIGS. 1A and 1B which can be adapted for anchoring the stent body 105 within the prostatic urethra and for preventing migration toward the bladder 112 (FIG. 2C). A tether 122 is provided for removing the stent 100 from the patient.

The stent body 105 can include a tubular member or sleeve with an outer everted sleeve portion 125 surrounding an inner body portion or sleeve portion 140 with the central passageway 110 extending therethrough. In FIGS. 1A and 1B, the stent body 105 is shown in a first insertion or deployed configuration where the everted sleeve portion 125 has an outer or first surface 142 that is configured to contact, grip and engage the walls of the prostatic urethra 106. As can be understood from FIGS. 1A-1 B, the everted sleeve portion 125 comprises a thin-wall elastomeric material (e.g., silicone). In this condition, the everted sleeve portion 125 has a rolling proximal end 143 which rolls over into the inner sleeve portion 140. In this variation, the inner sleeve portion 140 also comprises an elastomeric material that can include at least one spring element 144 therein for maintaining the stent body 105 in its cylindrical configuration following deployment to resist the radially-inward pressure of the prostatic urethra 106.

In one variation, the spring element 144 comprises a suitable helical spring although a number of spring configurations can be embedded in the wall 145 of the inner sleeve portion 140 to prevent its collapse. In some variations, the spring element 144 can be radially collapsible into a small cross-section to allow deployment from a smaller diameter catheter or introducer device where the spring element 144 expands the stent body 105 to the configuration shown in FIGS. 1A-1B after deployment from the catheter.

As can be understood from FIGS. 1A-1B, a variation of the stent body 105 includes projecting elements 146 or barb-like features in an outer or first surface 142 of the stent body 105 that engage tissue in walls of the lumen which resist any migration of the stent body 105. However, removal of the stent with such projecting elements would not be possible as the projecting elements would be engaging or penetrating tissue. Thus, the invention is configured to provide such projecting elements 146 in a surface 142 of the stent body 105 that can be inverted during removal so that the projecting elements face inwardly toward the interior passageway 110 and do not engage tissue. As described above, contractions of the prostate 108 often can cause a prostatic stent to migrate. In some variations of the current invention, any forces applied to the stent body 105 by the prostate 108 may simply cause partial inversion of the outer stent sleeve portion 125 carrying the projecting elements 146 rather than displacing the entire stent body 105.

Figure 1C:
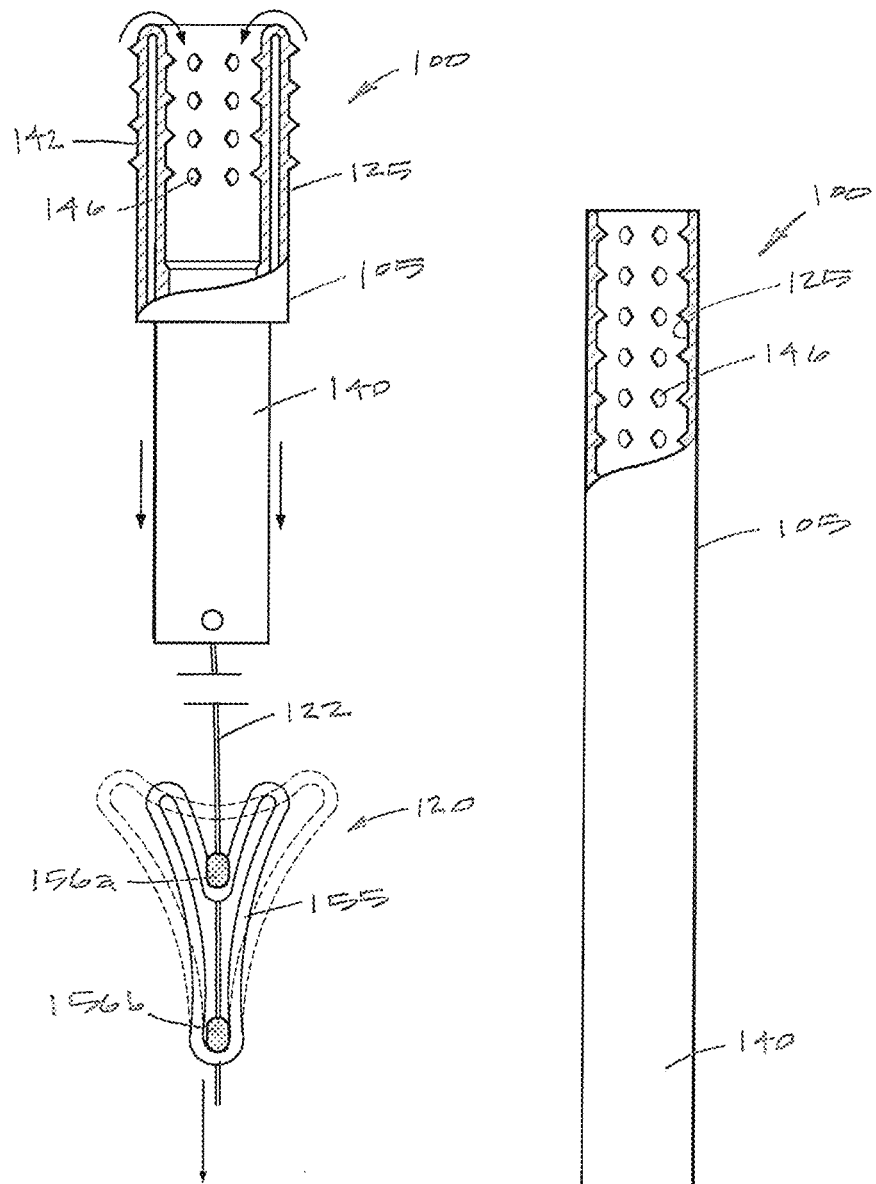
FIG. 1C is another cut-away view of the stent of FIG. 1A showing the everted outer sleeve portion partially inverted as when being removed from the patient's prostatic urethra.
Figure 1D:
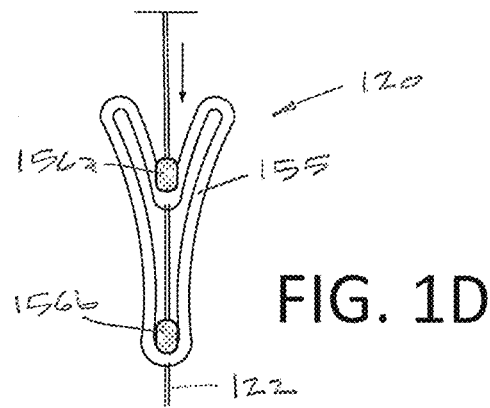
FIG. 1D is another view of the stent of FIGS. 1A-1C with the everted outer sleeve portion being completely inverted for removing the stent from the patient.

In FIG. 1A, it can be seen that an optional flexible anchor element 120 is provided which is adapted for collapse within the catheter 150 or introducer device as shown in FIGS. 1B, 2A and 5A. The anchor 120 is adapted to be positioned in the urethra distal to the external sphincter 116 of the prostate 108 and is adapted to open therein to prevent migration of the stent body toward the bladder 112. In one variation, the anchor 120 comprises a frame 155 of a resilient, bendable plastic that is inwardly collapsible as shown in FIG. 1B. The tether 122 is coupled to the inner sleeve portion 140 of the stent body 105, typically in 2 to 4 locations with branches of the tether. The tether has 122 anchor collars shown at 156a and 156b that are spaced apart so as to collapse the anchor frame 155 inwardly as distal forces on the anchor frame 155 are applied to the tether 122 to withdraw the stent body 105 from the patient's prostate. Now turning to FIGS. 1C and 1D, it can be seen how the everted portion 125 is adapted to invert when the tether 122 is pulled in the distal direction (outward relative to bladder 112) to remove the stent body 105 from the patient's prostate. In FIG. 1C, it can be seen that the everted sleeve portion 125 is partly inverted. In FIG. 1D, it can be seen that the initial everted sleeve portion 125 is entirely inverted and the stent body 105 is transformed into a elongated tubular member that can be easily withdrawn from the patient's prostate 108 without the projecting elements 146 engaging tissue. In any variation, the surfaces of the stent portions that interface one another can comprise a highly lubricious material or coating, such as a teflon or the like.

As can be seen in FIGS. 1A-1B, the first or outer surface 142 of the outer everted sleeve portion 125 carries the projecting elements 146 for engaging the walls the prostatic urethra 106. Such projecting elements 146 can consist of a plurality of polymer, elastomeric elements that are suitably stiff and/or sharp to grip, engage and/or penetrate tissue. Such projecting elements 146 also can comprise metal elements or barbs adapted to penetrate tissue that can be molded into the elastomeric sleeve. In any event, such projecting elements 146 are configured to allow for rolling or inversion of the everted sleeve portion 125 to an inverted configuration as will be further described below.

In general, a stent body 105 corresponding to the invention comprises an everted sleeve portion 125 that can be inverted into a tubular member wherein the projecting elements 146 in an exterior or first surface 142 in an everted configuration are adapted for engaging, gripping or penetrating tissue in a lumen to resist migrating forces within a patient's prostatic urethra, bulbous urethra or ureter. The stent body 105 comprises an elastomeric material which can be inverted by tension and movement of a tether 122 wherein the projecting elements 146 then face inwardly to allow simplified withdrawal of the stent body from the lumen. The stent body 105 can be made in more than one length and diameter which are adapted for different sized prostatic urethras of various patients, as well as other lengths and cross-sections suitable for a bulbous urethra or a ureter.

FIG. 2A shows a first step of a method of using the stent 100 where in the stent is loaded in the elongated flexible tubular catheter 150. In FIG. 2A, the catheter 150 is introduced through the patient's urethra into the bladder 112. Thereafter, a balloon 170 carried at a distal end 172 of the catheter 150 is inflated and then the catheter 150 is pulled the distal direction towards the internal sphincter 114 at the junction of the bladder 112 in the prostatic urethra 106. Thereafter, the catheter 150 is in position for deployment of the stent 100 in the prostatic urethra 106. FIGS. 2A-2B show deployment of the stent body 105 in the prostatic urethra 106 wherein an obturator sleeve 175 in the core of the catheter 150 is maintained in a fixed position and the outer catheter sleeve 180 is moved in the distal direction to thus deploy the stent body 105 and anchor 120 (FIG. 2C).

Figure 2E:
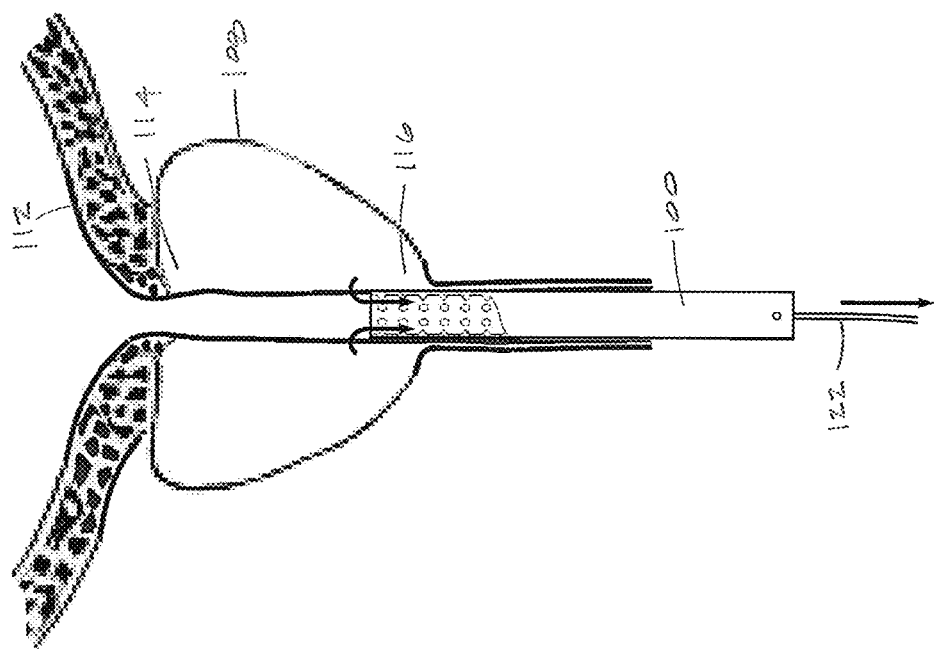
FIG. 2E shows further distal movement of the tether which inverts the stent for removal from the patient.

FIG. 2C shows the stent body 105 and anchor 120 deployed with the patient. FIG. 2D thereafter shows withdrawal of the stent 100 from the patient. In FIG. 2D, it can be seen that the movement of tether 122 in the distal direction unrolls and inverts the outer sleeve portion 125 as the anchor 120 and stent body 105 are withdrawn from the prostate. In FIG. 2E, it can be seen that further movement of the tether 122 fully inverts the previously everted sleeve portion 125 and the entire stent body 105 can be removed from the lumen.

Figure 3:
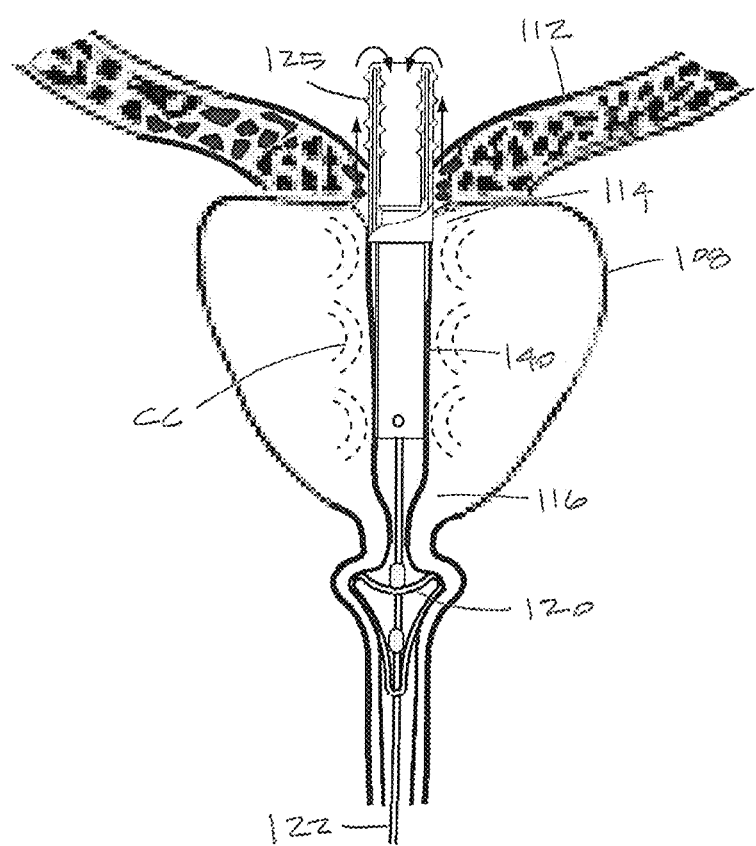
FIG. 3 shows the stent of FIGS. 1A and 2C with migrating forces applied to the stent by the prostate walls that may cause migration of the stent and in this case only moves the exterior sleeve of the stent in the proximal direction.

FIG. 3 schematically illustrates contractions CC within the prostate 108 which represent forces applied to the outer everted sleeve portion 125 that can cause a portion of the sleeve to invert. In this circumstance, such contractions CC could cause rolling and inverting of the outer sleeve portion 125 rather than causing the stent body to migrate altogether. In FIG. 3, it can be understood that rolling of the outer sleeve portion 125 would extend the sleeve further into the bladder 112 and would not alter the functionality of temporary stent.

Figure 4:
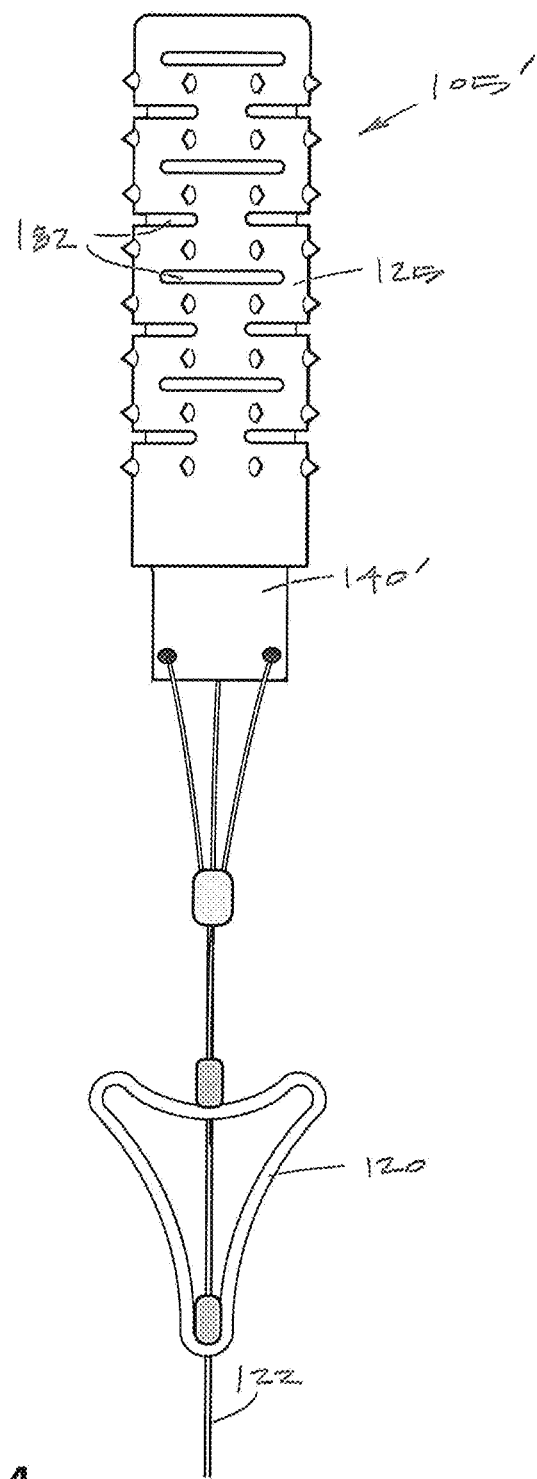
FIG. 4 shows a stent similar to that of FIG. 1A except the outer sleeve of the stent has apertures therein.

FIG. 4 shows another variation of a stent body 105' that is similar to that of FIGS. 1A-1B except that the outer sleeve portion 125' has a plurality of openings 182 therein which will assist in the drainage of urine from the patient's bladder 112 in the event the everting sleeve portion 125' partially inverts into the inner stent body portion 140' from prostatic contractions (see FIG. 4) and the sleeve portion 125' then projects inwardly into the patient's bladder 112.

Now turning to FIGS. 5A and 5B, the distal end of a catheter 150 or introducer is shown carried which is the same type as shown in FIGS. 2A-2B. It can be seen that the catheter 150 has an outer sleeve 180 carrying the positioning balloon 170 and an inner obturator sleeve that 175 engages the distal end 188 of the stent body 105'.

FIGS. 6A-6B illustrate another variation of the prostatic stent 200 that is similar to that of FIGS. 1A-1B as described previously except the stent body 205 when deployed has a bulged or bowed-outward medial portion 208 around axis 210 intermediate the proximal end 212 and distal end 214. The stent 200 again carries a plurality of projecting elements 215 for engaging tissue. The bulged shape (exaggerated in FIGS. 6A-6B) is adapted to further prevent migration of the stent body within the prostatic urethra. It is believed that such a bulged shape will resist migration and this variation again includes the rollable, outer everted sleeve portion 225. In this variation, the stent 200 is adapted for collapsing to a smaller pre-deployed diameter for carrying in a cylindrical bore of a catheter 150 (see FIG. 5A). In FIG. 6B, it can be seen that the inner stent body portion 240 is radially collapsible with a elastomeric helical elements 242 having embedded spring elements 244 with undulations making in radially collapsible. The stent body 205 of FIGS. 6A and 6B is shown deployed in a prostate in FIG. 7. In this variation, it is believed that a proximal anchor in the urethra (cf. FIG. 2C) is not needed as the projecting elements 215 and bulged medial portion 208 will prevent migration over a short interval of temporary use as described above. Withdrawal of the stent 200 is then similar to the method described previously where pulling distally on the tether 245 will cause the everted outer sleeve portion 225 to invert as the entire stent body 205 is withdrawn. Further, as the stent body 205 is being withdrawn, the inner stent body portion 240 with the helical configuration will collapse radially under tension as a helical configuration is stretched linearly axially from the bulged shape shown in FIGS. 6A-6B. Optional elastomeric webs 248 may extend between adjacent helical elements 242 to limit axial stretching of the inner stent body portion 240.

FIG. 6C illustrates another variation of a prostatic stent 200' that is similar to that of FIGS. 6A-6B. In this variation, the stent 200' includes a collar portion 255 that is adapted to extend into and engage the bladder wall at the internal sphincter as shown in phantom view in FIG. 7 to function as a proximal anchor in the bladder 112. The collar portion 255 comprises an elastomeric sleeve with a collapsible spring element 256 therein. It should be appreciated that additional anchor features can be provided in such a collar portion 255 such as an annular balloon (not shown) that an be inflated and deflated through a lumen in the stent wall as is known in the art.

FIG. 8 shows another variation of a stent 260 that is deployed in a patient's ureter 262 to treat a constriction or other disorder. The stent 260 is similar to that of FIGS. 1A-1B with tether 265 except that the stent 260 is highly elongated with a spring element to maintain an open passageway in its inner sleeve portion. This variation of stent 260 can be deployed with a catheter similar to the method shown in FIGS. 2A-2C and can be removed in a method similar to that shown in FIGS. 2D-2E. In another variation (not shown) a similar stent in a shorter length can be adapted for treating a stricture in a patient's bulbous urethra.

In the stent configurations shown above, the stent bodies are shown having a round cross-section. It should be appreciated that the cross-section can also be somewhat triangular shape which may better fit the natural cross-sectional shape of a patient's prostatic urethra. In such variations, the catheter can include markings to rotationally orient the stent prior to deployment.

FIGS. 9 and 10 illustrate another variation of stent 400 with interior passageway 402 that has a partially triangular cross-sectional shape and has a different form of inverting portion that carries projecting elements 405 for engaging tissue. In this variation, the stent 400 comprises an elastomeric material 406 with undulating spring elements 408 in wall portions 410a-410c thereof that allow for radial collapse of wall portions for carrying the stent in a small diameter catheter similar to that of FIGS. 2A-2B and FIGS. 5A-5B. Further, the stent 400 is adapted to be transformed into a smaller diameter for withdrawal with tear-way inverting wall portions or strips 415a-415c which carry the projecting elements 405. As can be understood in FIGS. 9 and 10, each inverting wall portion or strip 415a-415c extends longitudinally relative to axis 420 and has tear-away edges 422 that can comprise perforations 424 in the elastomeric material 406 or a thin tearable web or the like. Each inverting wall portion 415a-415c has a tether or pull-cord 425a-425c with a proximal end 426 thereof attached to a proximal end 428 of each inverting wall portion 415a-415c (see FIG. 9). FIG. 10 illustrates a tether 425a being pulled in the distal direction which causes wall portion 415a to invert and thereby disengage the projecting elements 405 from engaging tissue. FIG. 10 illustrates a single tether 425a inverting a single inverting wall portion 415a, but it should be appreciated that the three tethers 425a-425c can be merged into a single pull cord as shown in FIG. 4 to invert and tear away all three wall portions 415a-415c at the same time. Further, the three remaining wall portions 410a-410c can have tethers 432 attached thereto as shown in phantom view in FIGS. 9 and 10 for withdrawal thereof after removal of the tear-away, inverting wall portions 415a-415c. In another variation, the distal end 442 of each inverting wall portions 415a-415c can be coupled to the distal end 444 of each adjacent non-inverting wall portions 410a-410c (see FIG. 10) with a non-tear away structure so that continued withdrawal of the inverting wall portions 415a-415c will pull the remainder of the 400 stent distally and outwardly from a prostate. This variation also can have a bowed outward medial portion (not shown) as in the stent of FIG. 6A. In this variation, the number of tear-away inverting strips can vary from 1 to four or more and can be configured as longitudinal strips or can be a helical strip with a low pitch angle.

FIGS. 11A and 11B illustrate another variation of stent 450 with interior passageway 452 that is similar to previous embodiments where the projecting elements 455 are carried in an outer surface 456 of the inverting structure. In this variation, the unitary outer sleeve 460 carries the projecting elements 455. The outer sleeve 460 again comprises an elastomeric material with spring elements 470 therein that allow for radial compression of the stent for carrying in an introducer catheter. The stent 450 again has a bowed-out medial portion 474. In this variation the proximal end 480 of the stent 450 is adapted for inverting with a branched tether 482 attached to multiple anchors 484 of the inverting sleeve 460. In FIG. 11A, the tether 482 is also shown as folded against an interior wall of stent and can be detachably adhered to the interior wall with tear-away adhesives. Thus, it can be understood how distal movement of the tether 482 as shown in FIG. 11B can invert and remove the stent 450 from the patient's urethra in a manner described previously. In this variation, it should be appreciated that the spring elements 470 in walls of the stent are configured for radial expansion as well as configured for rolling into the inverting condition as the stent 450 is inverted and withdrawn from the patient. In general, the spring element or elements 470 can be circumferential with a short axial dimension or can be helical with a similar short width the can be rolled and inverted. In a variation, the spring elements 470 can further be configured with bends or attachments that comprise the projecting elements 455 that can be inverted. Such projecting portions of the spring elements 470 can be covered with the elastomeric material of the stent wall or can project outward from the wall to grip or penetrate tissue.

FIGS. 12A-12B illustrate another form of prostatic stent 500 that is similar to previous variations in that withdrawal of the stent following use is accomplished by inverting the tubular elastomeric sleeve 504 to disengage projecting elements 505 from the wall of the urethra. In this variation, deployment of the stent 500 is performed by rolling or everting the tubular sleeve 504 of the stent to thereby cause the projecting elements 505 to engage tissue. FIG. 12A shows the stent 500 in a partially inverted configuration with the projecting elements 505 facing radially inwardly which is the form of the stent when carried in a distal end of a catheter 510 (see FIG. 13A). It can be seen that the stent wall or sleeve 504 again has projecting elements 505 therein and spring elements 515 of the type described previously for maintaining an open passageway 520 in the stent 500. In this variation, at least one of the spring elements 515 is shown with a sharp barb portion 522 adapted to penetrate tissue.

FIG. 12B shows the stent 500 after being further everted wherein the projecting elements 505 now face radially outwardly for engaging tissue. In this variation, tethers 524a and 524b are shown coupled to a first end 525 of the stent which is a proximal end of the stent 500 in the deployed condition. It should be appreciated that multiple tethers can be provided for inverting the stent to uniformly pull the stent's proximal or first end 525 in the distal direction as a tethers 524a and 524b are pulled distally. As described previously, multiple tethers 524a and 524b can merge into a single tether (not shown). In FIGS. 12A-12B, it also can be seen that stent 500 has perforations 528 in a proximal portion 532 thereof for allowing urine flow from the bladder through the perforations 528 into the central passageway 520 of the stent when deployed.

FIG. 13A shows the stent 500 of FIG. 12A carried in the distal end of catheter 510. As can be seen in FIG. 13A, the catheter 510 has an outer sleeve 542 and a concentric translatable inner sleeve 544. Further, in this variation, an endoscope 550 is carried in the central passageway of the catheter 510 for viewing introduction of the stent 500 into the patient's prostate 108. In FIG. 13A, it can be seen that the endo scope 550 has a field of view FOV to allow observation of landmarks in the patient's prostate such as the external sphincter 116, verumontanum VM, internal sphincter 114 and bladder 112. The physician then can position the distal end 552 of the catheter 510 in a selected location such that everting the sleeve 504 of the stent 500 causes the projecting elements 505 to engage the prostatic urethra 106 in a desired location distal to the internal sphincter 114.

Now referring to FIG. 13B, the stent 500 can be deployed by the advancing the catheter inner sleeve 544 relative to outer sleeve 542 to thereby deploy and evert the sleeve 504 of the stent. FIG. 13C then shows stent 500 deployed with the projecting elements 505 engaging tissue with the catheter 510 removed. It can be seen that tethers 524a and 524b then extend through the urethra for later removal of the stent. FIG. 13D depicts the physician pulling distally on tethers 524a and 524b which thereby inverts the sleeve 504 to thereby disengage the projecting elements 505 from tissue after which the stent 500 can be removed as described previously.

While FIGS. 12A-13D illustrate a stent that is everted by unrolling or everting a sleeve of a stent in a proximal direction (i.e., toward the bladder 112), it should be appreciated that a similar unrolling stent (not shown) can be provided that everts in the distal direction to cause projecting elements to engaged tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A stent for treating a urologic disorder, comprising:
   a stent body having a deployed configuration with an outer surface portion having a plurality of projecting elements directed outward from the outer surface portion such that the plurality of projecting elements are configured to engage tissue in a wall of a lumen in a patient's urinary tract, wherein the stent body has a central passageway extending therethrough;
   a tether coupled to the stent body; and
   wherein the stent body is transformable to an inverted configuration in which the outer surface portion is configured to invert within an end of the stent causing movement of the projecting elements within the central passageway of the stent body which disengages the projecting elements from the tissue for withdrawal of the stent body from the lumen where application of a force on the tether causes transformation of the stent body from the deployed configuration to the inverted configuration.

2. The stent of claim 1 wherein the stent body is dimensioned for deployment in a lumen of a prostatic urethra, a ureter or a bulbous urethra.

3. The stent of claim 1 wherein distal movement of the tether is adapted to progressively roll and invert the outer surface portion to the inverted configuration.

4. The stent of claim 1 wherein at least a portion of the stent body comprises an elastomeric material.

5. The stent of claim 1 wherein the outer surface portion carrying the projecting elements comprises a tear-away portion.

6. The stent of claim 5 wherein the tether is coupled to the tear-away portion.

7. The stent of claim 1 wherein the stent body includes at least one spring element that reinforces the central passageway and prevents collapse thereof in the deployed configuration.

8. The stent of claim 7 wherein at least a portion of the spring element is in a helical configuration.

9. The stent of claim 7 wherein the spring element is radially-collapsible to allow radial compression of thereof.

10. The stent of claim 1 wherein the stent body has a cylindrical configuration about a central axis.

11. The stent of claim 1 wherein the stent body extends about an axis from a proximal end to a distal end and has an expanded cross section in a medial portion between the proximal and distal ends.

12. The stent of claim 1 wherein the stent body has a round cross-sectional shape.

13. The stent of claim 1 wherein the stent body has a partially triangular cross-sectional shape.

14. The stent of claim 1 wherein the stent body has a plurality of openings in a wall of the stent body.

15. A stent for positioning in a lumen of a patient to treat a urologic disorder, comprising:
   a stent body having an insertion configuration with an outer sleeve portion surrounding an inner body portion having a central passageway extending therethrough, where the stent body is dimensioned for insertion and deployment in a prostatic urethra, a ureter or a bulbous urethra;
   wherein the stent body is adaptable to an inverted configuration in which the sleeve portion rolls and inverts within the central passageway to allow for withdrawal from the lumen; and
   an elongated tether coupled to the inner body portion.

16. The stent of claim 15 wherein distal movement of the tether causes a progressive rolling of the sleeve portion to invert within the central passageway to assume the inverted configuration.

17. The stent of claim 15 wherein an exterior surface of the everted sleeve portion has at least one engagement feature that is configured to engage with a wall of a lumen.

18. A method of temporarily stenting a urinary tract lumen, comprising:
deploying a stent body in a urinary tract lumen for a treatment interval wherein an outer surface portion of the stent body carries projecting elements that engage a tissue in a wall of the urinary tract lumen; and
disengaging the projecting elements from tissue by pulling distally on a tether coupled to a portion of the stent body to cause the outer surface portion of the stent body to invert within the stent body such that the projecting elements face inwardly allowing for withdrawal of the stent body from the urinary tract lumen.

19. The method of claim 18 wherein disengaging the projecting elements from tissue inverts a tear-away outer surface portion of the stent body.

20. The method of claim 18 wherein disengaging the projecting elements from tissue inverts a sleeve portion of the stent body.

21. A method of treating a wall of a lumen to treat a urologic disorder, comprising:
providing a delivery catheter carrying a stent body having a insertion configuration with an outer surface carrying projecting elements that engage tissue in the wall of the lumen, the stent body having a passageway extending therethrough;
introducing a distal portion of the catheter into the lumen;
deploying the stent body from the catheter in the insertion configuration to create a temporary flow path through the stent passageway and lumen;
withdrawing the catheter from the lumen;
subsequent to a treatment interval, pulling distally on a tether coupled to a portion of the stent body to invert the outer surface portion carrying the projecting elements within the stent body allowing for disengaging the stent body from the lumen; and
withdrawing the stent body from the lumen after inverting the outer surface portion.

22. The method of claim 21 wherein introducing the distal portion includes expanding an expandable member carried at a distal end of the catheter in a patient's bladder and positioning the expandable member in the bladder proximate the internal sphincter.

23. The method of claim 21, further comprising collapsing the expandable member prior to withdrawing the catheter from the lumen.

24. The method of claim 21, where introducing the distal portion of the catheter into the lumen comprises introducing the distal portion into a prostatic urethra, a ureter or a bulbous urethra.

25. A stent for treating a urologic disorder, comprising:
a stent body having a deployed configuration with an outer surface portion having a plurality of projecting elements directed outward from the outer surface portion such that the plurality of projecting elements are configured to engage tissue in a wall of a lumen in a patient's urinary tract, wherein the stent body has a central passageway extending therethrough, wherein the stent body includes at least one spring element that reinforces the central passageway and prevents collapse thereof in the deployed configuration; and
wherein the stent body is transformable to an inverted configuration in which the outer surface portion is configured to invert within an end of the stent causing movement of the projecting elements within the central passageway of the stent body which disengages the projecting elements from the tissue for withdrawal of the stent body from the lumen.

26. The stent of claim 25 wherein the stent body is dimensioned for deployment in a lumen of a prostatic urethra, a ureter or a bulbous urethra.

27. The stent of claim 25 further comprising a tether coupled to the stent body such that application of a force on the tether causes transformation of the stent body from the deployed configuration to the inverted configuration.

28. The stent of claim 25 wherein distal movement of the tether is adapted to progressively roll and invert the outer surface portion to the inverted configuration.

29. The stent of claim 25 wherein at least a portion of the stent body comprises an elastomeric material.

30. The stent of claim 25 wherein the outer surface portion carrying the projecting elements comprises a tear-away portion.

31. The stent of claim 30 wherein the tether is coupled to the tear-away portion.

32. The stent of claim 25 wherein at least a portion of the spring element is in a helical configuration.

33. The stent of claim 25 wherein the spring element is radially-collapsible to allow radial compression of thereof.

34. The stent of claim 25 wherein the stent body has a cylindrical configuration about a central axis.

35. The stent of claim 25 wherein the stent body extends about an axis from a proximal end to a distal end and has an expanded cross section in a medial portion between the proximal and distal ends.

36. The stent of claim 25 wherein the stent body has a round cross-sectional shape.

37. The stent of claim 25 wherein the stent body has a partially triangular cross-sectional shape.

38. The stent of claim 25 wherein the stent body has a plurality of openings in a wall of the stent body.

39. A stent for treating a urologic disorder, comprising:
a stent body having a deployed configuration with an outer surface portion having a plurality of projecting elements directed outward from the outer surface portion such that the plurality of projecting elements are configured to engage tissue in a wall of a lumen in a patient's urinary tract, wherein the stent body has a central passageway extending therethrough and wherein the stent body has a partially triangular cross-sectional shape; and
wherein the stent body is transformable to an inverted configuration in which the outer surface portion is configured to invert within an end of the stent causing movement of the projecting elements within the central passageway of the stent body which disengages the projecting elements from the tissue for withdrawal of the stent body from the lumen.

* * * * *